(12) United States Patent
Banchieri et al.

(10) Patent No.: US 12,213,681 B2
(45) Date of Patent: Feb. 4, 2025

(54) END EFFECTOR POSITIONING MECHANISM

(71) Applicant: AtriCure, Inc., Mason, OH (US)

(72) Inventors: Michael J. Banchieri, Discovery Bay, CA (US); Matthew Monti, Cincinnati, OH (US); Tamer Ibrahim, Danville, CA (US); Kenneth L. Miller, Hamilton, OH (US); Ara M. Stephanian, Davis, CA (US); Dwight P. Morejohn, Davis, CA (US)

(73) Assignee: AtriCure, Inc., Mason, OH (US)

( * ) Notice: Subject to any disclaimer, the term of this patent is extended or adjusted under 35 U.S.C. 154(b) by 76 days.

(21) Appl. No.: 17/308,435

(22) Filed: May 5, 2021

(65) Prior Publication Data

US 2021/0346030 A1    Nov. 11, 2021

Related U.S. Application Data

(60) Provisional application No. 63/020,612, filed on May 6, 2020.

(51) Int. Cl.
  *A61B 17/128*    (2006.01)
  *A61B 17/00*     (2006.01)

(52) U.S. Cl.
  CPC .............. *A61B 17/1285* (2013.01); *A61B 2017/00314* (2013.01)

(58) Field of Classification Search
  CPC .... A61B 2017/003; A61B 2017/00305; A61B 2017/00309; A61B 2017/00314; A61B 2017/00318; A61B 2017/00323; A61B 2017/00327; A61B 2017/00331; A61B 2017/2908; A61B 2017/320071; A61B 17/1285; A61B 1/00149; A61B 1/008
  See application file for complete search history.

(56) References Cited

U.S. PATENT DOCUMENTS

| | | |
|---|---|---|
| 8,636,754 B2 | 1/2014 | Hughett, Sr. et al. |
| 9,017,349 B2 | 4/2015 | Privitera et al. |
| 9,861,371 B2 | 1/2018 | Martin et al. |
| 9,883,867 B2 | 2/2018 | Martin et al. |
| 9,901,351 B2 | 2/2018 | Winkler et al. |
| 9,901,352 B2 | 2/2018 | Fago et al. |
| 10,201,352 B2 | 2/2019 | Fago et al. |

(Continued)

*Primary Examiner* — Shaun L David
*Assistant Examiner* — Rachael L Geiger
(74) *Attorney, Agent, or Firm* — Dorton & Willis LLP; Ryan Willis

(57) ABSTRACT

An end effector positioning mechanism for a surgical device may include an articulation mechanism including a plurality of tiltable segments disposed generally in a longitudinal row between an elongated shaft of a surgical device and an end effector of the surgical device. Each of the plurality of segments may be generally in the form of a flattened disk. At least one of the segments may include a proximal surface and/or a distal surface that is substantially planar and is oriented substantially orthogonally with respect to a central axis of the articulation mechanism. At least one of the segments may include a proximal surface and/or a distal surface including two transversely oriented, generally planar surfaces that meet along a substantially diametric peak.

6 Claims, 8 Drawing Sheets

(56) References Cited

U.S. PATENT DOCUMENTS

| | | | |
|---|---|---|---|
| 2007/0276430 A1* | 11/2007 | Lee | A61B 1/00071 606/205 |
| 2012/0289946 A1* | 11/2012 | Steger | A61B 34/30 606/1 |
| 2014/0039387 A1* | 2/2014 | Kim | A61B 17/3421 604/95.04 |
| 2015/0047451 A1* | 2/2015 | Kwon | A61B 17/29 74/490.05 |
| 2017/0095922 A1* | 4/2017 | Licht | A61B 34/71 |
| 2019/0142428 A1 | 5/2019 | Widenhouse et al. | |
| 2019/0231329 A1* | 8/2019 | Xu | A61B 17/00234 |

\* cited by examiner

END EFFECTOR POSITIONING MECHANISM

CROSS REFERENCE TO RELATED APPLICATION

This application claims the benefit of U.S. Provisional Application No. 63/020,612, filed May 6, 2020, which is incorporated by reference.

INTRODUCTION TO THE INVENTION

The present disclosure is directed to surgical instruments and devices and related methods, and, more specifically, to mechanisms for rotating and/or articulating end effectors of surgical devices, and related methods.

The present disclosure contemplates that atrial fibrillation is a common heart arrhythmia, affecting millions of people in the United States. In some patients with atrial fibrillation, stagnant blood in the heart's left atrial appendage ("LAA") may be a source of blood clots, which may enter the blood circulation and increase the risk of stroke. Excluding the LAA, which may create electrical and/or fluidic isolation of the LAA, may be beneficial in terms of reducing the atrial fibrillation burden and/or reducing the risk of stroke for some patients. Accordingly, in some patients, it may be desirable to exclude the LAA by securely sealing the LAA orifice at the base of the LAA using an occlusion clip. Typically, an occlusion clip is releasably attached to an end effector of a clip applier. The present disclosure contemplates that difficulties encountered in left atrial appendage exclusion procedures may include challenges in precisely positioning the occlusion clip at the desired location on the left atrial appendage using the clip applier. This difficulty may be particularly relevant when the heart is accessed in a minimally invasive manner, such as via a small sub-xiphoid or sub-costal incision. The present disclosure contemplates that the difficulty of positioning an occlusion clip on the left atrial appendage may be reduced by utilizing a clip applier having an end effector that is repositionable, such as rotatable and/or articulatable. Similarly, the difficulty of other surgical procedures may be reduced by utilizing a surgical device having an end effector that is rotatable and/or articulatable.

While known devices have been used safely and effectively, the present disclosure contemplates that improvements in the construction and operation of clip appliers and other surgical devices including end effectors may be beneficial for users (e.g., surgeons) and patients. Accordingly, the present disclosure includes various improvements which may enhance the construction, operation, and methods of use of surgical devices including rotatable and/or articulatable end effectors.

It is an aspect of the present disclosure to provide an end effector positioning mechanism for a surgical device including an articulation mechanism which may include a plurality of tiltable segments disposed generally in a longitudinal row between an elongated shaft of a surgical device and an end effector of the surgical device.

In a detailed embodiment, each of the plurality of segments may be generally in the form of a flattened disk. At least one of the segments may include at least one of a proximal surface and a distal surface that is substantially planar and is oriented substantially orthogonally with respect to a central axis of the articulation mechanism.

In a detailed embodiment, at least one of the segments may include at least one of a proximal surface and a distal surface comprising two transversely oriented, generally planar surfaces that meet along a substantially diametric peak. The segment may have a first thickness proximate the peak and a second thickness orthogonally distant from the peak. The first thickness may be greater than the second thickness.

In a detailed embodiment, each of the plurality of segments may be oriented at about 90 degrees of rotation about a central axis of the articulation mechanism compared to at least one adjacent segment.

In a detailed embodiment, at least one of the segments may include at least one longitudinal hole. At least one of the segments may include a plurality of longitudinal holes disposed generally circumferentially evenly spaced apart proximate an outer periphery of the segment. The end effector positioning mechanism may include at least one tension line extending through at least one of the longitudinal holes. When the tension line is tensioned, at least one gap between adjacent segments may become smaller, thereby articulating the articulation mechanism.

In a detailed embodiment, when the tension line is tensioned, at least one of the segments may be tilted towards the tension line. Each of the segments may be substantially similar to the other segments. At least one of the segments may differ from one or more of the other segments.

In a detailed embodiment, the end effector positioning mechanism may include a rotation mechanism configured to facilitate rotation of the end effector about an end effector longitudinal axis. The rotation mechanism may include a bearing assembly.

It is an aspect of the present disclosure to provide a surgical device including an elongated shaft, a handle disposed at a proximal end of the shaft, and/or an end effector disposed at a distal end of the shaft. The end effector may be articulable with respect to a shaft longitudinal axis. The end effector may be rotatable about an end effector longitudinal axis. The end effector may be rotatable about the shaft longitudinal axis.

In a detailed embodiment, a surgical device may include an end effector positioning mechanism including an articulation mechanism and a rotation mechanism. The articulation mechanism may include a pivotable connection mounting the end effector to the shaft. A surgical device may include an actuator disposed on the handle, the actuator being operable to articulate the end effector about the pivotable connection. The rotation mechanism may be operable by an actuator disposed on the handle to rotate the end effector about the end effector longitudinal axis. The actuator disposed on the handle to rotate the end effector may include a hub rotatably disposed on the handle about the shaft longitudinal axis. A surgical device may include a torque tube extending longitudinally through the shaft generally coaxially with the shaft longitudinal axis from the hub to the end effector.

It is an aspect of the present disclosure to provide a method of using a surgical device including articulating an articulation mechanism of a surgical device by tensioning a tension line. The articulation mechanism may include a plurality of tiltable segments disposed generally in a longitudinal row between an elongated shaft of the surgical device and an end effector of the surgical device. Each of the plurality of segments may be generally in the form of a flattened disk. The tension line may extend through respective longitudinal holes of the plurality of segments. When the tension line is tensioned, at least one gap between adjacent ones of the plurality of segments may become smaller, thereby articulating the articulation mechanism.

In a detailed embodiment, tensioning the tension line may include tilting at least one of the plurality of segments towards the tension line. At least one of the plurality of segments may include at least one of a proximal surface and a distal surface comprising two transversely oriented, generally planar surfaces that meet along a substantially diametric peak. The segment may have a first thickness proximate the peak and a second thickness orthogonally distant from the peak. The first thickness may be greater than the second thickness. Tensioning the tension line may tilt the plurality of segments to reduce a gap between adjacent ones of the plurality of segments proximate the second thickness orthogonally distant from the peak.

BRIEF DESCRIPTION OF THE DRAWINGS

Example embodiments are described in conjunction with the accompanying drawing figures in which.

DETAILED DESCRIPTION

Example embodiments according to the present disclosure are described and illustrated below to encompass devices, methods, and techniques relating to medical procedures. Of course, it will be apparent to those of ordinary skill in the art that the embodiments discussed below are examples and may be reconfigured without departing from the scope and spirit of the present disclosure. It is also to be understood that variations of the example embodiments contemplated by one of ordinary skill in the art shall concurrently comprise part of the instant disclosure. However, for clarity and precision, the example embodiments as discussed below may include optional steps, methods, and features that one of ordinary skill should recognize as not being a requisite to fall within the scope of the present disclosure.

The present disclosure includes, inter alia, surgical instruments and devices and related methods, and, more specifically, mechanisms for rotating and/or articulating end effectors of surgical devices, and related methods. Some example embodiments according to at least some aspects of the present disclosure may be particularly useful in connection with clip appliers, such as clip appliers that may be used to apply occlusion clips to left atrial appendages.

Figure 1:
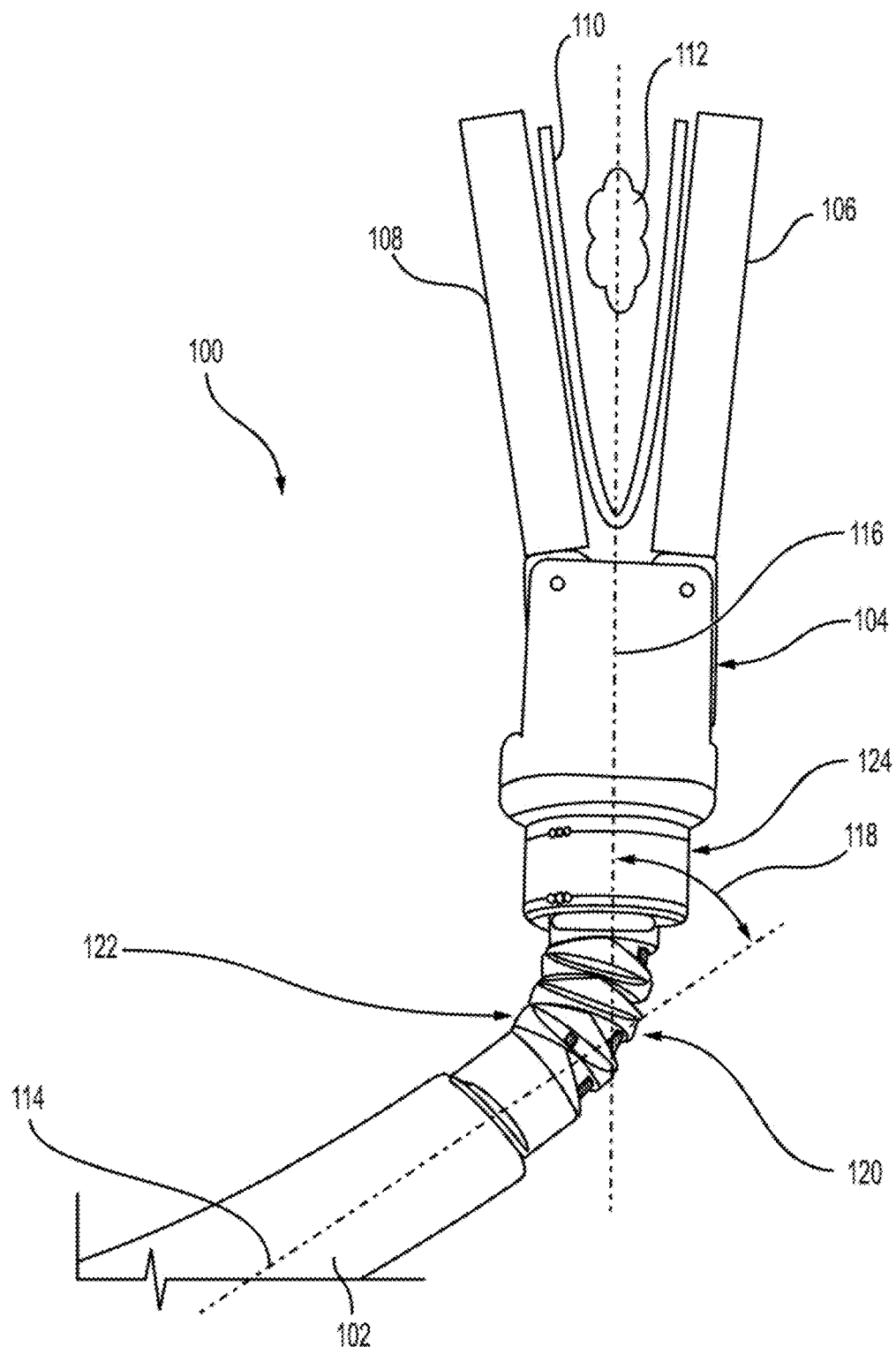
FIG. 1 is an elevation view of an example clip applier.
Figure 2:
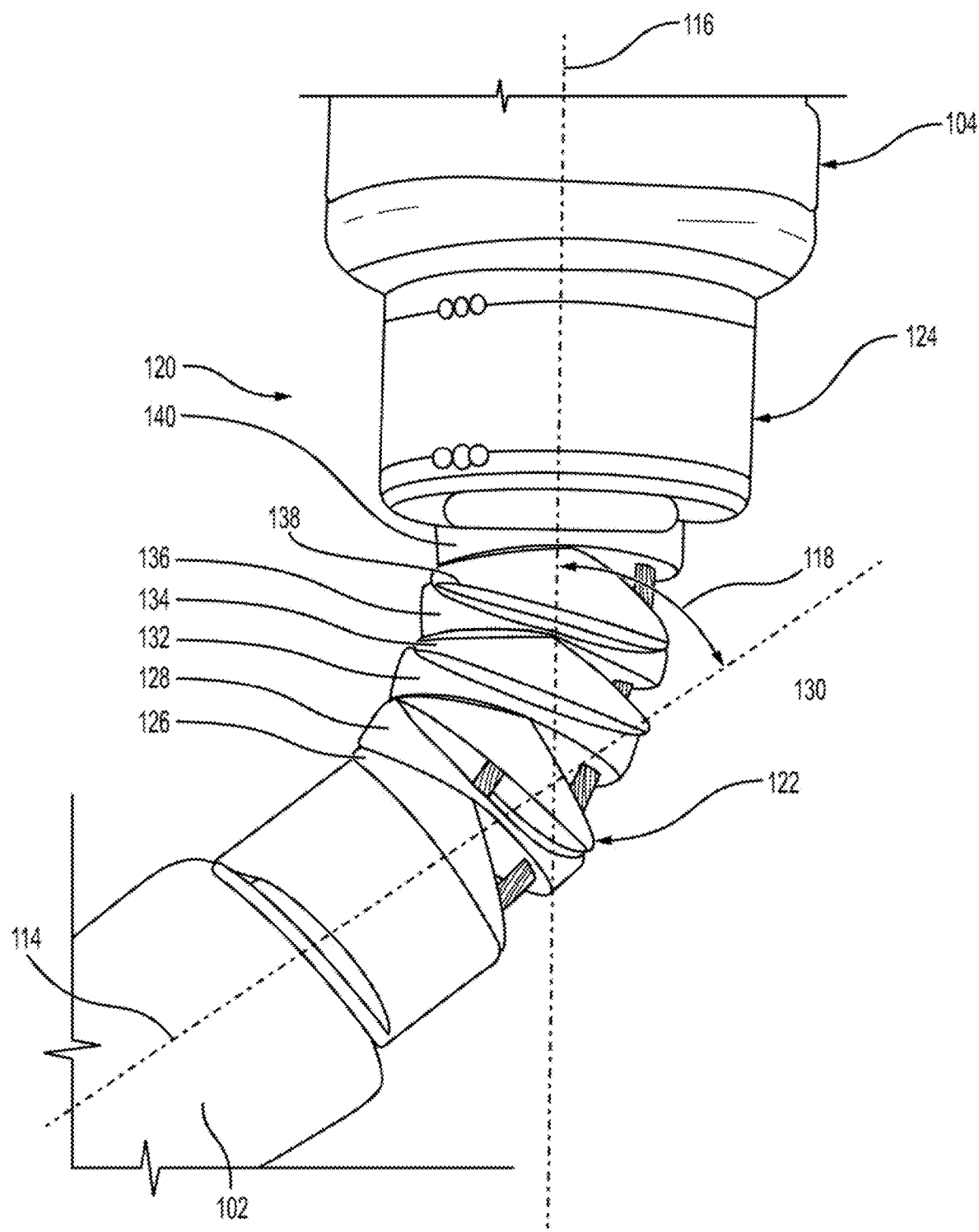
FIG. 2 is a detailed elevation view of an end effector positioning mechanism in an articulated configuration.
Figure 3:
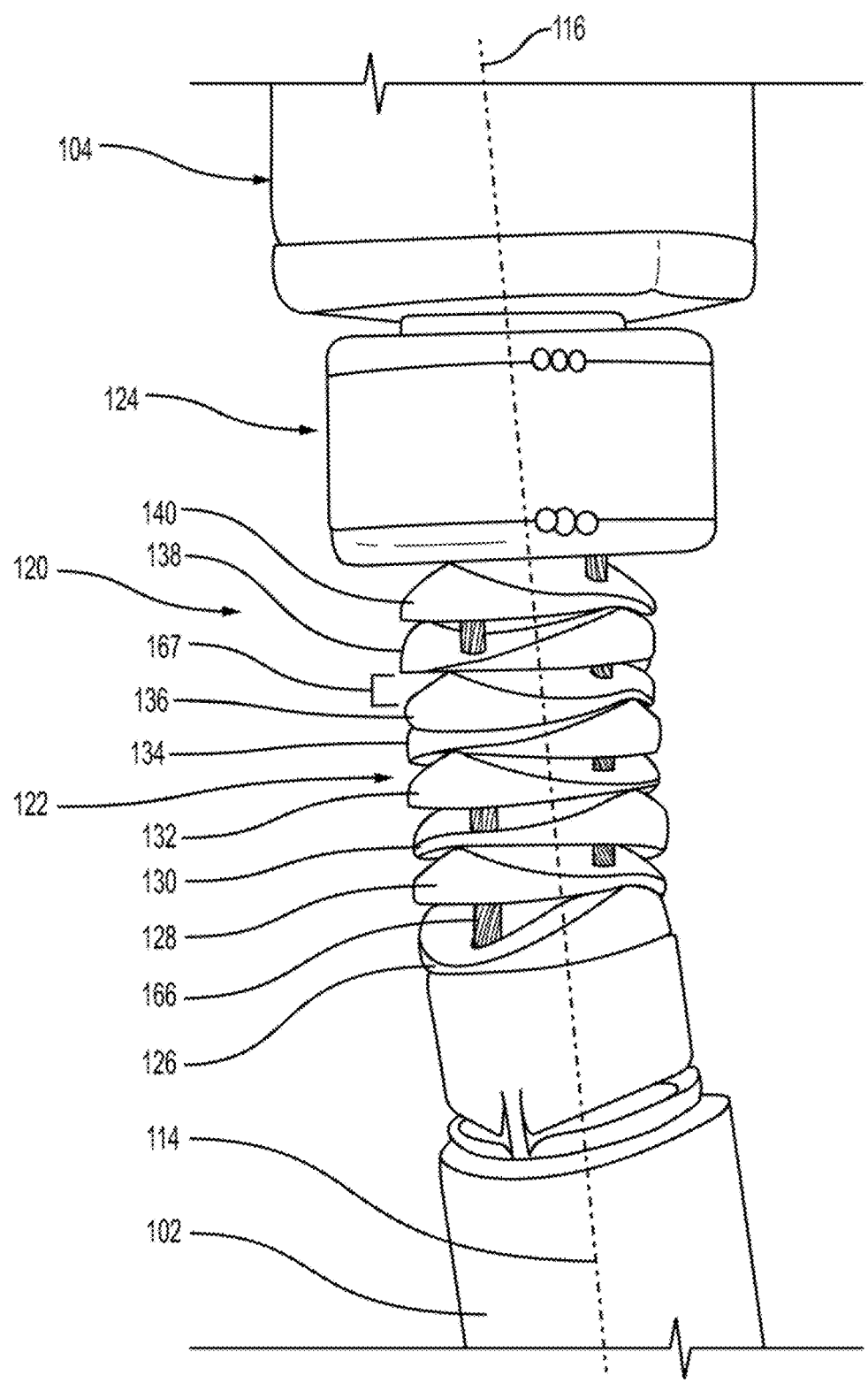
FIG. 3 is a detailed elevation view of the end effector positioning mechanism of FIG. 2 in a generally straight configuration.
Figure 4:
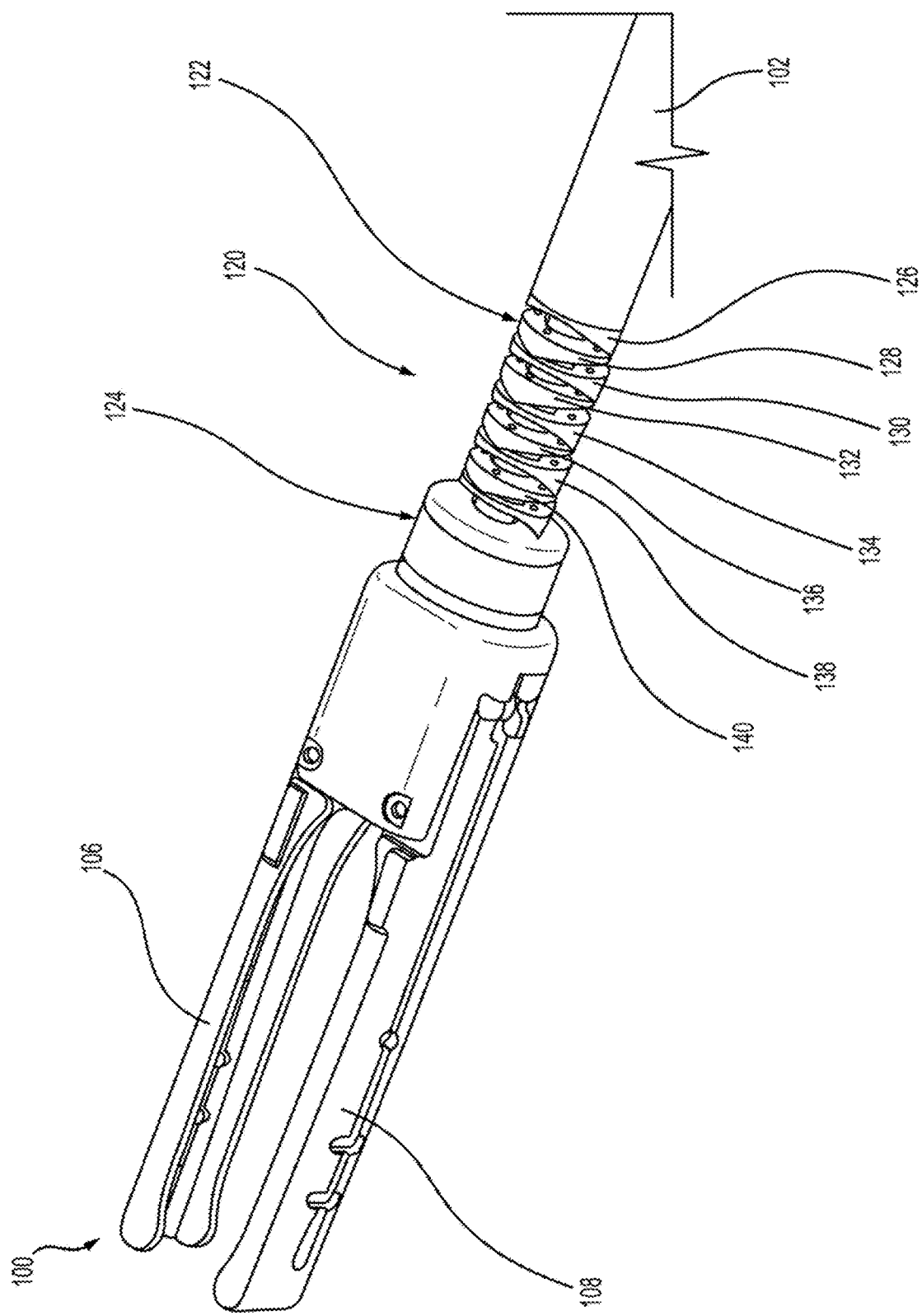
FIG. 4 is an isometric view of the clip applier of FIG. 1.
Figure 5:
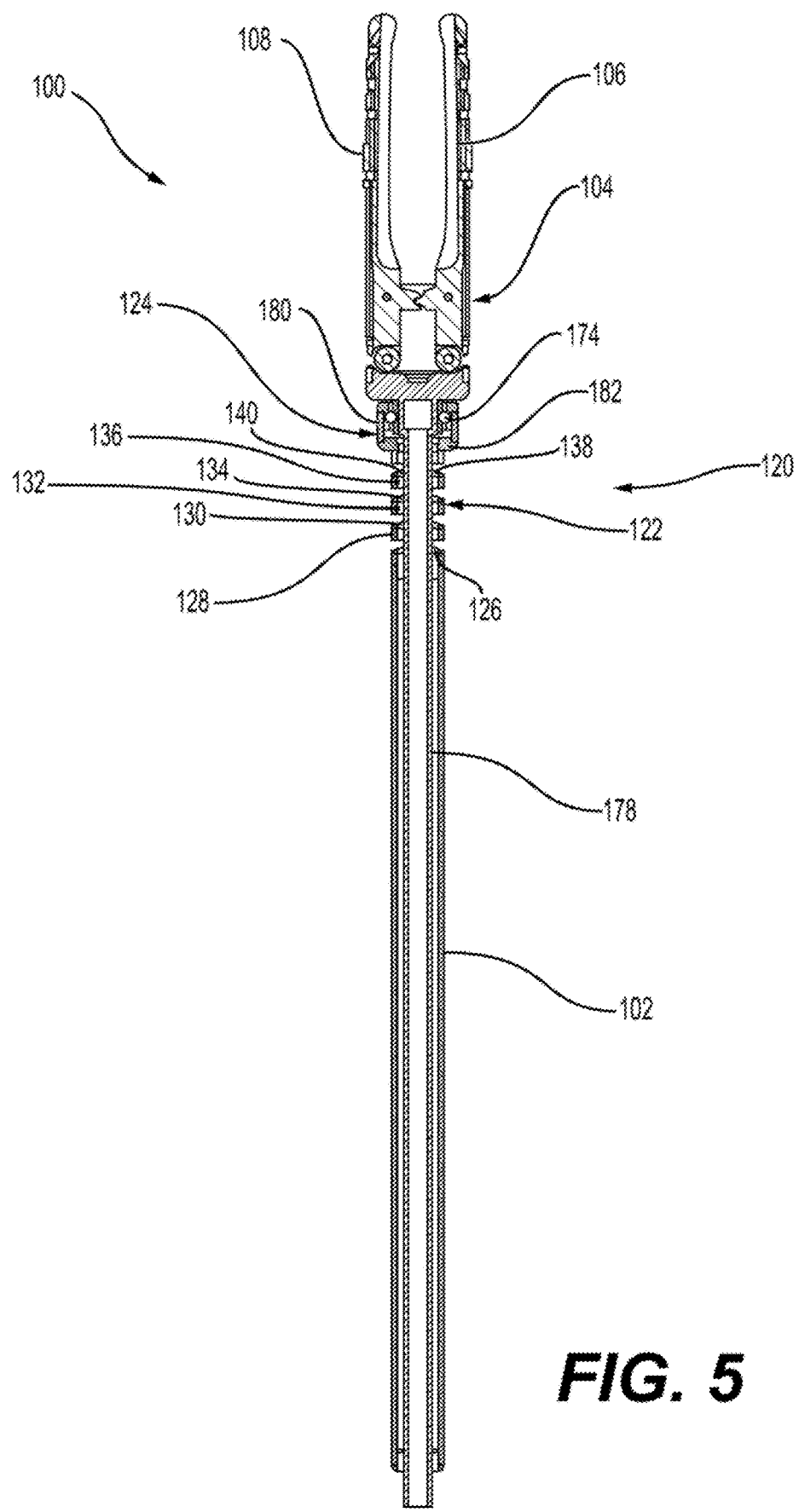
FIG. 5 is a cross-section view of the clip applier of FIG. 1.

FIG. 1 is an elevation view of an example surgical device, such as a clip applier 100, FIG. 2 is a detailed elevation view of an end effector positioning mechanism 120 in an articulated configuration, FIG. 3 is a detailed elevation view of the end effector positioning mechanism 120 in a generally straight configuration, FIG. 4 is an isometric view of the clip applier 100, and FIG. 5 is a cross-section view of the clip applier 100, all according to at least some aspects of the present disclosure. Referring to FIGS. 1-5, the clip applier 100 may include an elongated shaft 102, a handle (not shown) disposed at a proximal end of the shaft 102, and/or an end effector 104 disposed at a distal end of the shaft 102. The shaft 102 may malleable or flexible, or it may be substantially rigid. In other embodiments, the shaft 102 may be steerable. The end effector 104 may include, for example, a pair of articulating jaws 106, 108 which may be configured to releasably hold an occlusion clip 110. The occlusion clip 110 may be configured for placement on a target tissue, such as a left atrial appendage 112 of a heart. For example, the occlusion clip 110 may include the PRO V clip available from AtriCure, Inc., of Mason, Ohio. U.S. Pat. Nos. 8,636,754; 9,017,349; 9,861,371; 9,883,867; 9,901,351; 9,901,352; and 10,201,352; and U.S. Patent Application Publication No. 2019/0142428, relate to LAA occlusion devices and methods and are incorporated by reference herein.

The shaft 102 may include a shaft longitudinal axis 114. The end effector 104 may include an end effector longitudinal axis 116. In some example embodiments, the end effector 104 may be articulatable (e.g., pivotable) with respect to the shaft longitudinal axis 114 so that the end effector longitudinal axis 116 is disposed at an angle 118 with respect to the shaft longitudinal axis 114. In various example embodiments, the end effector 104 may be articulatable with respect to the shaft longitudinal axis 114 in one or more planes. In some example embodiments, the end effector 104 may be rotatable about the end effector longitudinal axis 116.

Generally, the articulation and/or rotation of the end effector 104 may be facilitated by an end effector positioning mechanism 120, which may interpose the shaft 102 and the end effector 104. In some example embodiments, the end effector positioning mechanism 120 may include an articulation mechanism 122 and/or a rotation mechanism 124.

Figure 6:
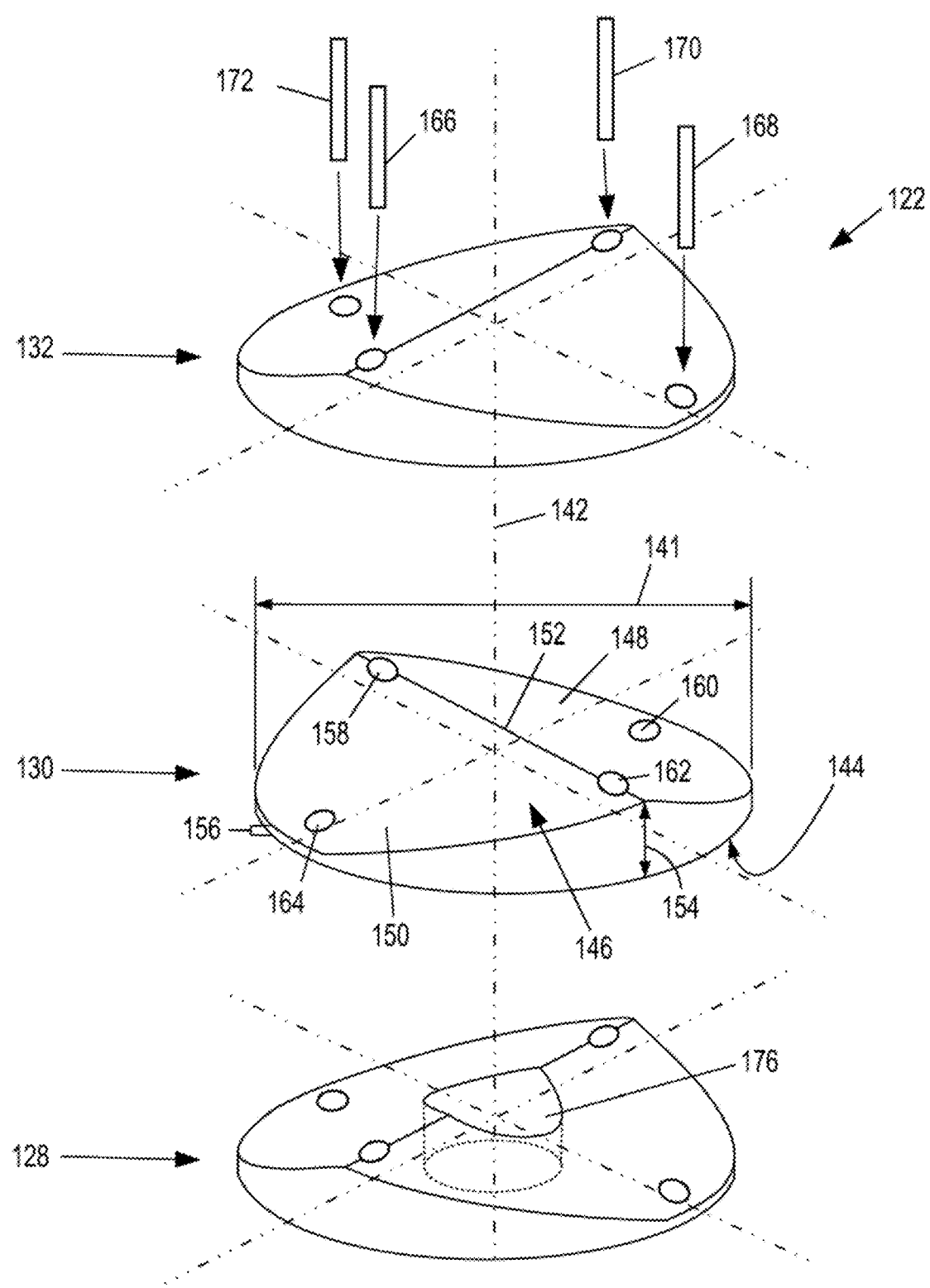
FIG. 6 is an exploded view of a portion of an articulation mechanism.
Figure 7:
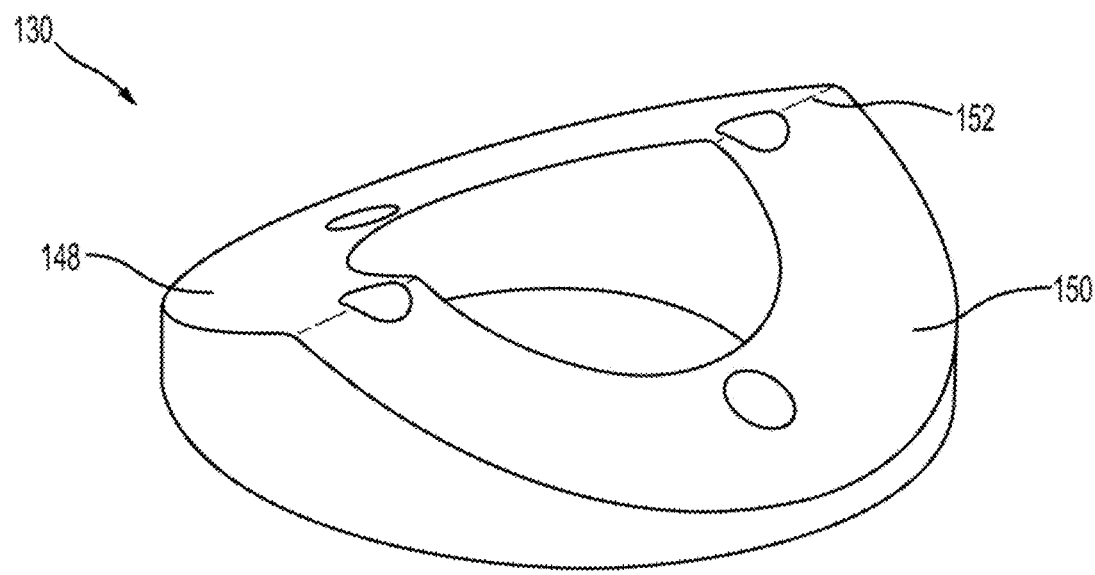
FIG. 7 is an isometric view of a segment.
Figure 8:
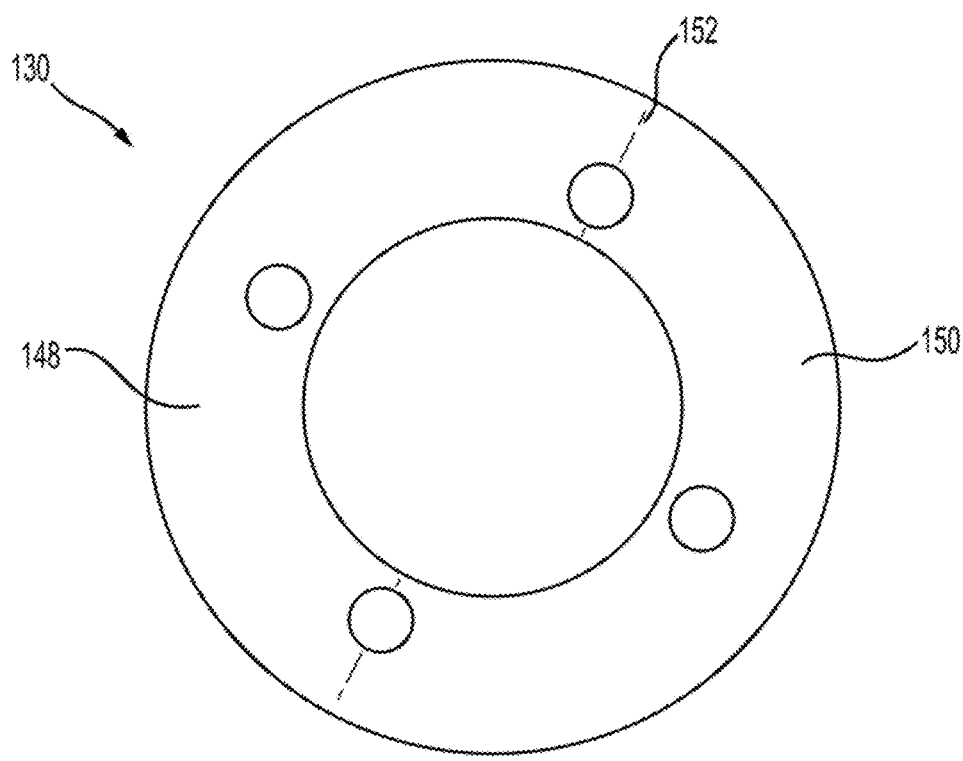
FIG. 8 is a plan view of the segment of FIG. 7.

FIG. 6 is an exploded view of a portion of the articulation mechanism 122, FIG. 7 is an isometric view of a segment 130, and FIG. 8 is a plan view of the segment 130, all according to at least some aspects of the present disclosure.

Referring to FIGS. 1-8, an example articulation mechanism 122 may include a one or more segments 126, 128, 130, 132, 134, 136, 138, 140, which may be disposed generally in a longitudinal row (e.g., proximally/distally with respect to each other). In this example embodiment, each of the segments 126, 128, 130, 132, 134, 136, 138, 140 is substantially similar to the other segments 126, 128, 130, 132, 134, 136, 138, 140; however, in other example embodiments, one or more of the segments 126, 128, 130, 132, 134, 136, 138, 140 may differ from one or more of the other segments 126, 128, 130, 132, 134, 136, 138, 140. The proximal-most segment 126 may be disposed on the distal end of the shaft 102. Generally, increasing the number of segments 126, 128, 130, 132, 134, 136, 138, 140 in the row will increase the maximum angle 118 to which the end effector 104 may be articulated. Generally, reducing the number of segments 126, 128, 130, 132, 134, 136, 138, 140 in the row will decrease the maximum angle 118 to which the end effector 104 may be articulated.

Referring to FIGS. 6-8, an example segment 130 is described in detail. It will be appreciated that, in this example embodiment, the other segments 126, 128, 132, 134, 136, 138, 140 may be substantially similar in structure and/or function. The segment 130 may be generally in the form of a flattened disk having a diameter 141 and a central axis 142. The proximal surface 144 of the segment 130 may be substantially planar and/or may be oriented substantially orthogonally with respect to the central axis 142. The distal surface 146 of the segment 130 may include two transversely oriented, generally planar surfaces 148, 150 that meet along a substantially diametric peak 152. For example, the surfaces 148, 150 of the distal surface 146 may be disposed at about 22.5 degrees with respect to the proximal surface 144. In other example embodiments, the surfaces 148, 150 of the distal surface 146 may be disposed at a greater angle with respect to the proximal surface 144, facilitating greater articulation, or the surfaces 148, 150 of the distal surface 146 may be disposed at a lesser angle with respect to the proximal surface 144, facilitating less articulation. The surfaces 148, 150 of the distal surface 146 may be arranged so that the thickest portion of the segment 130 (e.g., in the longitudinal/proximal-distal direction) lies along the peak 152, where the segment 130 has a first thickness 154. The thinnest portions of the segment 130 may be where the surfaces 148, 150 intersect the circular perimeter of the segment 130 at positions generally orthogonally distant from the peak 152, where the segment 130 has a second thickness 156. The first thickness 154 may be greater than the second thickness 156.

The segment may include a plurality of longitudinal through bores, such as holes 158, 160, 162, 164. The holes 158, 160, 162, 164 may be disposed generally circumferentially evenly spaced apart and/or near the outer periphery of the segment 130. For example, two holes 158, 162 may extend through the peak 152 and/or two holes 160, 164 may extend through the segment 130 at positions orthogonally distant from the peak 152. Generally, the segment 130 may be substantially symmetrical about the peak 152.

Referring to FIGS. 1-8, the articulation mechanism 122 may be assembled so that each segment 126, 128, 130, 132, 134, 136, 138, 140 is oriented at about 90 degrees of rotation about the central axis 142 with respect to the adjacent segment(s) 126, 128, 130, 132, 134, 136, 138, 140. Referring to FIG. 6, a tension line 166 may extend longitudinally through the holes 158, 160, 162, 164 of the segments 126, 128, 130, 132, 134, 136, 138, 140. Because of the alternating orientations of the segments 126, 128, 130, 132, 134, 136, 138, 140, the tension line 166 may extend through hole 164 of segment 126, hole 162 of segment 128, hole 164 of segment 130, hole 162 of segment 132, etc. Accordingly, the tension line 166 may extend alternately through the thick portions and the thin portions of segments 126, 128, 130, 132, 134, 136, 138, 140. In FIG. 3, the tension line 166 is visible in gaps 167 between the proximal surfaces 144 and the sloped distal surfaces 146 of adjacent segments 126, 128, 130, 132, 134, 136, 138, 140.

The tension line 166 may be secured distally, such as to the end effector 104 and/or the rotation mechanism 124. Accordingly, upon tensioning the tension line 166, such as from the handle at the proximal end of the shaft 102, the gaps 167 between the adjacent segments 126, 128, 130, 132, 134, 136, 138, 140 may become smaller. This may tilt the segments 126, 128, 130, 132, 134, 136, 138, 140 generally toward the tension line 166, which may articulate the end effector 104 generally toward the tension line 166 as shown in FIG. 2.

Referring to FIG. 6, in this example embodiment, the articulation mechanism 122 includes four tension lines 166, 168, 170, 172, one corresponding to each of the holes 158, 160, 162, 164 through the segments 126, 128, 130, 132, 134, 136, 138, 140. Accordingly, the articulation mechanism 122 may be articulated (e.g., tilted) in any of the four directions corresponding to the four tension lines 166, 168, 170, 172 by tensioning the respective tension line 166, 168, 170, 172. Tensioning two adjacent tension lines 166, 168, 170, 172 may allow the articulation mechanism 122 to articulate generally in a direction between the two tensioned tension lines 166, 168, 170, 172.

Referring to FIGS. 6-8, in some example embodiments, the segments 126, 128, 130, 132, 134, 136, 138, 140 may include a longitudinal channel 176. For clarity, the channel 176 is shown only on segment 128 in FIG. 6; however, any segment 126, 128, 130, 132, 134, 136, 138, 140 may include a similar channel 176. In some example embodiments, one or more wires or other actuator members (e.g., a torque tube) may extend from within the shaft 102, through the channels 176, and to the rotation mechanism 124 and/or the end effector 104, such as to facilitate articulation of the jaws 106, 108, deployment of the occlusion clip 110, etc. For example, a jaw opening/closing cable may extend longitudinally from the handle to the end effector 104 via the internal lumen of the shaft 102 and/or the channels 176 of the segments 126, 128, 130, 132, 134, 136, 138, 140.

Although the example embodiment illustrated in FIGS. 1-8 includes segments 126, 128, 130, 132, 134, 136, 138, 140 having substantially flat proximal surfaces 144 and sloped distal surfaces 146, other embodiments within the scope of this disclosure may include alternative configurations. For example, one or more of the segments may include a substantially flat distal surface and a sloped proximal surface. In other embodiments, both the proximal and distal surfaces may be sloped. In other embodiments, a sloped surface may include a single slope extending diametrically across the segment, rather than two sloped surfaces meeting at a central peak.

Referring to FIGS. 1-5, the rotation mechanism 124 may interpose the articulation mechanism 122 and the end effector 104. The rotation mechanism 124 may include a bearing assembly 174 that facilitates rotation of the end effector 104 about its longitudinal axis 116. For example, the bearing assembly 174 may comprise a ball bearing having an inner race coupled to the end effector 104 and/or an outer race coupled to the distal portion of the articulation mechanism 122. Rotation of the end effector 104 about its longitudinal axis 116 may be controlled from the handle. For example, a torque tube 178 may extend from the handle to the rotation mechanism 124, such as within and/or coaxial with the shaft 102. The torque tube 178 may be rotatable with respect to the shaft 102. The torque tube 178 may comprise a laser-cut hypotube and/or may be coupled for rotation with the end effector 104. The torque tube 178 may be generally flexible in bending to facilitate shaft flexibility while having sufficient rotational stiffness to allow control of the rotation of the end effector 104 relative to the shaft 102. The rotation mechanism 124 may include a sleeve 180 around the bearing assembly 174 and a proximal plate 182. The plate 182 may include holes corresponding to the tension lines 166, 168, 170, 172, which may receive and secure the tension lines 166, 168, 170, 172 distally. For example, each hole may have a distal counter-bore that seats a cable ball affixed to the distal end of the respective tension line.

Referring to FIGS. 1-3, the end effector positioning mechanism 120 including the articulation mechanism 122 and/or the rotation mechanism 124 may allow the end effector 104 to articulate in substantially any plane parallel with the shaft longitudinal axis 114 (e.g., 360 degree articulation) and/or may allow the end effector to rotate to any angle about the end effector longitudinal axis 116. Accordingly, the clip applier 100 including the end effector positioning mechanism 120 may facilitate positioning of the occlusion clip 106, such as on a left atrial appendage.

Figure 9:
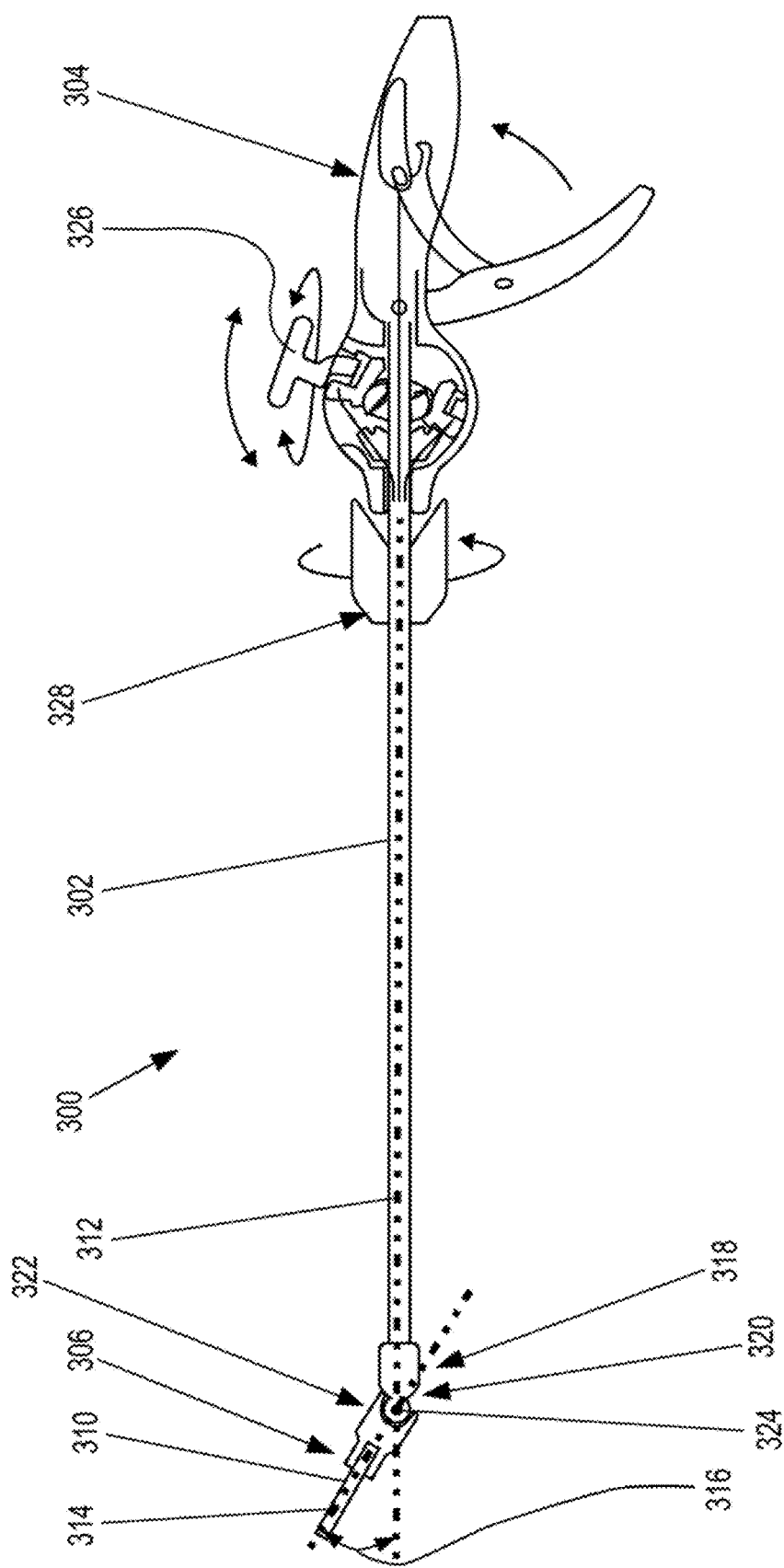
FIG. 9 is an elevation view of an example surgical device; all in accordance with at least some aspects of the present disclosure.

FIG. 9 is an elevation view of an example surgical device 300, according to at least some aspects of the present disclosure. The surgical device may include an elongated shaft 302, a handle 304 disposed at a proximal end of the shaft 302, and/or an end effector 306 disposed at a distal end of the shaft 302. The shaft 302 may malleable or flexible, or it may be substantially rigid. In other embodiments, the shaft 302 may be steerable. The end effector 306 may include, for example, a pair of articulating jaws 308, 310 which may be configured to releasably hold an occlusion clip. The occlusion clip may be configured for placement on a target tissue, such as a left atrial appendage of a heart. For example, the occlusion clip may include the PRO V clip available from AtriCure, Inc., of Mason, Ohio.

The shaft 302 may include a shaft longitudinal axis 312. The end effector 306 may include an end effector longitudinal axis 314. In some example embodiments, the end effector 306 may be articulatable (e.g., pivotable) with respect to the shaft longitudinal axis 312 so that the end effector longitudinal axis 314 may be pivoted at an angle 316 with respect to the shaft longitudinal axis 312. In various example embodiments, the end effector 306 may be articulatable with respect to the shaft longitudinal axis 312 in one or more planes, the end effector 306 may be rotatable about the end effector longitudinal axis 314, and/or the end effector 306 may be rotatable about the shaft longitudinal axis 312.

Generally, the articulation and/or rotation of the end effector 306 may be facilitated by an end effector positioning mechanism 318, which may be generally similar to end effector positioning mechanism 120 and/or which may include an articulation mechanism 320 and/or a rotation mechanism 322. The articulation mechanism 320 may include a pivotable connection 324 by which the end effector 306 is mounted to the shaft 302. The end effector 306 may be articulated about the pivotable connection 324 by moving an actuator 326, which may be disposed on the handle 304. For example, the actuator 326 may be pivoted to articulate the end effector 306. The rotation mechanism 322 may allow the end effector 306 to be rotated about the shaft longitudinal axis 312 by rotating the hub 328 on the handle 304, such as by rotating the actuator 326.

In some example embodiments, the hub 328 may be operatively connected to the end effector positioning mechanism 318 to rotate the end effector 306 about the shaft longitudinal axis 312. For example, the shaft 302 may be slotted to allow for a pin to connect the hub 328 to a torque tube, which may be generally similar to the torque tube 178 described above. When the hub 328 is rotated, the pin couples that rotational motion to the torque tube. The torque tube is coupled to the inner race of the bearing assembly (e.g., similar to bearing assembly 174) at the distal end, and that inner race is also connected to the distal end effector 306. The outer race of the bearing assembly is connected to the shaft 302, which may not rotate relative to the handle 304.

Following from the above description and invention summaries, it should be apparent to those of ordinary skill in the art that, while the methods and apparatuses herein described constitute example embodiments according to the present disclosure, it is to be understood that the scope of the disclosure contained herein is not limited to the above precise embodiments and that changes may be made without departing from the scope as defined by the following claims. Likewise, it is to be understood that it is not necessary to meet any or all of the identified advantages or objects disclosed herein in order to fall within the scope of the claims, since inherent and/or unforeseen advantages may exist even though they may not have been explicitly discussed herein.

What is claimed is:

1. A surgical device comprising:
an elongated shaft,
a handle disposed at a proximal end of the shaft, and
an end effector disposed at a distal end of the shaft;
wherein the end effector is articulable with respect to a shaft longitudinal axis using a plurality of tiltable segments, where each segment includes a planar proximal-most stationary surface and a distal diametric and linearly extending peak, where the planar proximal-most stationary surface of a first segment is configured to teeter on the distal diametric peak of a second adjacent segment;
wherein consecutive distal diametric and linearly extending peaks are rotationally offset by ninety degrees;
wherein the end effector is rotatable about an end effector longitudinal axis; and
wherein the end effector is rotatable about the shaft longitudinal axis.

2. The device of claim 1, further comprising an end effector positioning mechanism, the end effector positioning mechanism comprising an articulation mechanism and a rotation mechanism.

3. The device of claim 2, wherein the articulation mechanism comprises a pivotable connection mounting the end effector to the shaft.

4. The device of claim 3, further comprising an actuator disposed on the handle, the actuator being operable to articulate the end effector about the pivotable connection.

5. The device of claim 2, wherein the rotation mechanism is operable by an actuator disposed on the handle to rotate the end effector about the end effector longitudinal axis.

6. The device of claim 1, wherein:
each of the plurality of tiltable segments includes a plurality of longitudinal holes disposed generally proximate an outer periphery thereof; and
each of the plurality of longitudinal holes is occupied by at least one tension line extending therethrough.

* * * * *